United States Patent [19]

Hermolin et al.

[11] Patent Number: 4,918,253

[45] Date of Patent: Apr. 17, 1990

[54] PROCESS FOR THE PREPARATION OF 1,2,5,6,9,10-HEXABROMOCYCLODODECANE

[75] Inventors: Joshua Hermolin, Ramat Hasharon; Amiram Groweiss, Herzlia; Aaron R. McMurray, Haifa, all of Israel

[73] Assignee: Bromine Compounds Limited, Israel

[21] Appl. No.: 201,547

[22] Filed: Jun. 2, 1988

[30] Foreign Application Priority Data

Jun. 11, 1987 [IL] Israel ......................................... 82858

[51] Int. Cl.$^4$ ........................ C07C 17/02; C07C 23/00
[52] U.S. Cl. .................................. 570/231; 570/239; 570/246
[58] Field of Search ................ 570/186, 246, 247, 231

[56] References Cited

U.S. PATENT DOCUMENTS

| | | | |
|---|---|---|---|
| 3,558,727 | 1/1971 | Jenkner et al. | 570/246 |
| 3,833,675 | 9/1974 | Newcombe et al. | 570/246 |
| 4,783,563 | 11/1988 | Taniuchi et al. | 570/246 |

FOREIGN PATENT DOCUMENTS

| | | | |
|---|---|---|---|
| 3447631 | 7/1986 | Fed. Rep. of Germany | 570/246 |
| 13762 | 10/1969 | Japan | 570/246 |

*Primary Examiner*—Werren B. Lone
*Attorney, Agent, or Firm*—Lerner, David, Littenberg, Krumholz & Mentlik

[57] ABSTRACT

1,2,5,6,9,10-Hexabromocyclododecane (HBCD) is prepared in an anhydrous process in polar solvents, by the bromination of 1,5,9-cis, trans, trans-cyclododecatriene at relatively high temperatures.

16 Claims, No Drawings

PROCESS FOR THE PREPARATION OF 1,2,5,6,9,10-HEXABROMOCYCLODODECANE

The present invention relates to a process for the preparation of 1,2,5,6,9,10-Hexabromocyclododecane (HBCD). More particularly, the present invention is directed to a substantially anhydrous process for preparing HBCD by the bromination of 1,5,9-cis, trans, trans-cyclododecatriene (CDT) in polar solvents, at relatively high temperatures and with very low solvent and bromine losses.

HBCD is a well known flame retardant agent, suitable for incorporation into various plastics, especially polystyrene resins. As with other flame retardant additives, HBCD must fulfil several basic requirements, such as melting range, color stability under processing conditions—or, in other words, it must remain colorless in order not to impart an undesired color to the article into which it is incorporated—and it may contain only a restricted amount of contaminants and impurities, such as bromides. Therefore, although the reaction of CDT with bromine to yield HBCD is easily carried out in the laboratory over a broad range of operating conditions, the quality and economic requirements of the product pose very strict limitations on the industrial production of HBCD.

Preparation of HBCD has been carried out in different solvents, such as acetic acid, carboxylic acids, halogenated hydrocarbons such as carbon tetrachloride, lower alcohols and their mixtures with other solvents. The preferred solvent for the bromination of CDT found so far is a solvent comprising a lower alcohol.

Bromination of CDT leads to the production of three different isomers of HBCD, having different physical properties, as well as to side-reactions such as allylic bromination, dehydrobromination and bromination of the solvent. The quality of the HBCD—as often happens with products which are a mixture of a number of different compounds—is therefore very dependent on the conditions employed for the preparation of the product.

The art has tried to overcome the problem of obtaining HBCD having uniform properties in several ways. EP 0 037 895, for example, teaches to recycle part of the solvent remaining after the solid has been separated, the bleed of mother liquor being at least 10%. This bleed is necessary, when operating according to the abovementioned patent, in order to remove part of the HBr which remains in the mother liquor and which would otherwise accumulate.

The art has also tried to provide means for removing HBr and the residual $Br_2$ from the product. For instance, excess bromine can be removed by treatment of the mother liquor with $NaHSO_3$, $NH_4OH$, $NH_4HCO_3$, $(NH_4)_2CO_3$ and CDT. The HBr can be removed by treating the mother liquor with $K_2CO_3$, $NaHCO_3$, $CaCO_3$, NaOH, $Na_2CO_3$, $NH_4OH$, $NH_4HCO_3$, $(NH_4)_2CO_3$, epoxides and derivatives of ethanolamine. All the above treatments present severe drawbacks in that they either produce $H_2O$, or form wastes that must be disposed of. The generation of $H_2O$ in the reaction medium is deleterious to the process, inasmuch as water, which accumulates in the system, lowers both the yield and the quality of HBCD. DE 3,447, 631 teaches the use of $Cl_2$ to convert HBr into nascent $Br_2$ which reacts with CDT. This patent, however, does not solve the major problem of acid accumulation in the mother liquor and further adds the additional drawback of the presence of chlorinated impurities in the product.

Furthermore, the art teaches to employ reaction temperatures which do not exceed 40° C., and which are usually much lower (10°–30° C.).

In one instance (DE 30 13 002) there is disclosed that the process claimed can be carried out in a continuous manner. This patent, however, exemplifies only a semibatch process which results in low throughputs, as is apparent to a person skilled in the art. However, when the process of the abovementioned German patent is attempted in a continuous mode, no industrially useful results are obtained, since continuous fouling of the reactor walls and accessories, as well as plugging of the pipelines, is experienced.

It has now been found, and this is an object of the invention, that it is possible to prepare HBCD by the bromination of CDT at relatively elevated temperatures, without the need for any purification or intentional solvent bleed.

It has further been found, and this is another object of the invention, that is possible to carry out all required neutralization steps, to remove excess bromine and HBr, while maintaining a substantially anhydrous environment in the mother liquor.

The process for the preparation of 1,2,5,6,9,10-Hexabromocyclododecane (HBCD) is characterized in that bromine and 1,5,9-cis, trans, trans-cyclododecatriene (CDT) are reacted in a suitable solvent and the reaction mixture is contacted with $NH_3$ after the bromination reaction is substantially concluded.

According to a preferred embodiment of the invention, the reaction mixture remaining after reaction with $NH_3$ is fed to a filtration step and the mother liquor remaining after filtration is employed in a subsequent reaction, without any purification treatment. This recycled mother liquor is employed together with make-up quantities of solvent to account for solvent losses during operation.

In a preferred embodiment of the invention $NH_3$ is provided in gaseous form. According to another preferred embodiment of the invention, $NH_3$ is provided in a solution in a suitable solvent other than water, preferably in the solvent in which the bromination reaction is carried out.

The residual $Br_2$ and the HBr which is formed in the reaction, react with $NH_3$ to give $NH_4Br$ which is insoluble and is filtered off together with the product. Removal of $NH_4Br$ from the product can then be achieved by washing, by means known to the man of the art.

According to a preferred embodiment of the invention, the solvent is a lower alcohol, preferably selected from ethanol, n-propanol and n-butanol According to another preferred embodiment of the invention, the reaction temperature is between 40° C. to 60° C. A temperature of about 50° C. has been found to be convenient when operating according to the process of the invention.

The relatively high temperature, besides providing a higher bromination rate, is also of importance in avoiding fouling of the reactor and accessories, which is a commonly experienced phenomena when high HBCD production rates are attempted. However, as will be apparent to a person skilled in the art, bromination at lower temperatures is possible although this involves renouncing the aforesaid advantages or part thereof.

The bromination step and the reaction with $NH_3$ can be carried out in different modes, known to the expert engineer, such as semi-continuous and continuous modes. For instance, all steps can be carried out in semi-batch operation in a single reactor. In this case, after the bromination reaction is concluded, NH₃ is fed to the reaction mixture and the resulting neutralized mixture is discharged to a filtration step. The mother liquor recovered from the filtration step is re-fed to the reactor, together with a make-up amount of fresh solvent, to replace solvent trapped in the filter cake. This continuous recycle results in substantially quantitative yields of the process, after steady-state operation has been attained.

Whenever it is desired to separate the bromination step and the reaction with $NH_3$, the reaction mixture is passed into a second reactor to which gaseous $NH_3$ is fed. These operations can be effected in any convenient way, as will be apparent to a person skilled in the art, e.g., in a semi-batch or in a continuous manner.

1,2,5,6,9,10-Hexabromocyclododecane, whenever prepared by the process of the invention, also forms part of the present invention. This product is characterized by a melting point higher than 178° C. and a Br⁻ content lower than 0.05%.

The above and other characteristics and advantages of the invention will be better understood through the following illustrative and nonlimitative example.

EXAMPLE

A 500 l glass-lined Schwelmer reactor (4 HP motor; 35-130 rpm agitator speed) equipped with an external recirculation pump (external recycle: 1 m³/h) was charged with 200 l of ethanol and the temperature was raised to about 50° C. Bromine feed (about 90 kg/h) and CDT feed (about 30 kg/h) were started. The reactor contents were maintained at a temperature of 50° C.±2° C. throughout the reaction stage (1.25 hours).

On completion of the reaction the reaction mixture (product slurry) was cooled to about 40° C. and gaseous ammonia was introduced through a dip pipe positioned adjacent to the impeller. The amount of NH₃ required (about 1.0 kg) was determined by the pH of the recirculating slurry, and was stopped when the pH reading reached 6-7. The temperature of the reaction mixture was maintained at about 40° C. throughout the neutralization step. After the ammonia feed was stopped, the contents of the reactor were fed to a centrifuge (Ellerwerk Model 935 H) with a filtration area of 0.83 m², operating at about 650 rpm. The reactor was emptied in three filtration cycles. The mother liquor leaving the centrifuge was returned to the reactor for the subsequent cycle, together with fresh ethanol as a make-up.

The results of thirteen production cycles, with recycle of mother liquor, are given in Table I. The total amount of solvent employed during these cycles was 200 l of the original ethanol to which additional 229 l of ethanol were added during the 13 cycles to maintain the total volume of mother liquor at the 200 l level.

Typical results obtained are as follows: Average content of solvent trapped in the wet HBCD cake (as determined by the amount of makeup required and HBCD produced): <10 wt%. NH₄Br content in the wet HBCD cake: ~5 wt%. Bromine and Br⁻ content in the HBCD powder (after washing and drying): Br: ≧73.9%; Br⁻: <500 ppm. Overall process yield based on CDT: >98%.

The content of the three different isomers of HBCD (referred to as HBCD-1, HBCD-2 and HBCD-3; m.p.=208°-210° C.; 169°-170° C.; and 171°-173° C., respectively) in the mother liquor was measured by HPLC analysis as follows. 1.5 g solution were dissolved in dioxane. The solution was analysed on a Zorbax ODS 4.6 mm×25 cm column using CH₃CN-H₂O (85:15) as the eluent. The UV detector was tuned on 230 nm. Pure samples of each of the three HBCD isomers were used as standards.

The above description and examples have been provided for the purpose of illustration and are not intended to be limitative. Many variations can be carried out in the process of the invention. For instance, different solvents may be employed; different types of flow reactors can be used or batch or semi-batch operations can be employed, all without exceeding the scope of the invention.

TABLE I

Summary of HBCD Production Cycles

| Batch No. | Make-up EtOH (l) | Total CDT (kg) | Total Br₂ (kg) | m.p.[2] (°C.) | ρ (g/cm³) | NH₄Br₂ (wt %) | HBCD-1 (wt %) | HBCD-2 (wt %) | HBCD-3 (wt %) |
|---|---|---|---|---|---|---|---|---|---|
| | | | | Mother Liquor Composition | | | | | |
| 1 | 0 | 45.1[1] | 138.0 | 179-190 | 0.874 | 2.83 | 2.4 | 3.6 | 4.6 |
| 2 | 20 | 37.8 | 116.0 | 180-191 | 0.914 | 2.79 | 2.7 | 5.0 | 4.4 |
| 3 | 15 | 37.8 | 116.0 | 180-191 | 0.938 | 2.76 | 3.0 | 5.6 | 5.6 |
| 4 | 20 | 37.8 | 116.0 | 178-190 | 0.939 | 2.78 | 3.2 | 5.5 | 6.5 |
| 5 | 20 | 37.8 | 116.0 | 180-191 | 0.945 | 2.83 | 3.3 | 5.9 | 6.2 |
| 6 | 15 | 37.8 | 116.0 | 178-190 | 0.965 | 2.78 | 3.2 | 7.5 | 6.3 |
| 7 | 24 | 37.8 | 116.0 | 178-190 | 0.970 | 2.67 | 3.9 | 7.8 | 6.9 |
| 8 | 18 | 37.8 | 116.0 | 178-189 | 0.983 | 2.78 | 3.7 | 8.5 | 6.4 |
| 9 | 15 | 37.8 | 116.0 | 178-189 | 0.985 | 2.83 | 3.7 | 9.2 | 7.0 |
| 10 | 15 | 37.8 | 116.0 | 179-190 | 0.990 | 2.82 | 3.5 | 7.8 | 7.0 |
| 11 | 13 | 37.8 | 116.0 | 179-191 | 0.996 | 2.75 | 3.8 | 8.2 | 7.8 |
| 12 | 18 | 37.8 | 116.0 | 178-190 | 0.990 | 2.78 | 3.9 | 7.7 | 8.5 |
| 13 | 19[3] | 37.8 | 116.0 | 178-190 | 0.992 | 2.84 | 3.9 | 7.7 | 8.3 |

[1]Batch duration: 1.5 H.
[2]After washing and drying.
[3]20 l of EtOH were added to the final mother liquor to fill up to 200 l.

What we claim is:

1. A process for the preparation of 1,2,5,6,9,10-Hexabromocyclododecane comprising reacting substantially to completion a reaction mixture comprising bromine and 1,5,9-cis, trans, trans-cyclododecatriene in a solvent,
   contacting said reaction mixture with substantially anhydrous NH₃ after substantial completion of said reaction said HBr is deposited therefrom as NH₄Br; and
   recovering said solvent substantially free of HBr.

2. A process according to claim 1, wherein said NH₃ comprises gaseous NH₃.

3. A process according to claim 1, wherein said NH$_3$ comprises a solution of NH$_3$ in a non-aqueous solvent.

4. A process according to claim 3, wherein said non-aqueous solvent is said reaction mixture solvent.

5. The process of claim 1, wherein said solvent is a lower alcohol.

6. The process of claim 5, wherein said lower alcohol is selected from the group consisting of ethanol, n-propanol and n-butanol.

7. 1,2,5,6,9,10-Hexabromocyclododecane, prepared according to the process of claim 1.

8. The process of claim 1, further comprising the step of returning said recovered solvent to said reacting step.

9. The process of claim 8, wherein said recovered solvent is returned to said reacting step more than once.

10. The process of claim 1, further comprising the step of providing a reaction mixture of said bromine, said 1,5,9-cis, trans, trans-cyclododecatriene and said solvent in a reactor prior to reacting said bromine with said 1,5,9-cis, trans, trans-cyclododecatriene in said solvent.

11. The process of claim 10, wherein said NH$_3$ is contacted with said reaction mixture in said reactor after said reaction is substantially completed.

12. The process of claim 10, wherein said reactor is a first reactor, said process further comprising the step of transferring said reaction mixture to a second reactor after said reaction is substantially completed, and contacting said NH$_3$ with said reaction mixture in said second reactor.

13. The process of claim 1, further comprising the steps of recovering said 1,2,5,6,9,10-Hexabromocyclododecane and said NH$_4$Br after said solvent is recovered, and washing said recovered 1,2,5,6,9,10-Hexabromocyclododecane and said NH$_4$Br is removed and essentially pure 1,2,5,6,9,10-Hexabromocyclododecane is recovered.

14. The process of claim 1, wherein said solvent is a polar organic solvent.

15. The process of claim 1, wherein said solvent substantially free of HBr is recovered by filtration.

16. The process of claim 1, wherein the bromination reaction temperature is between 40° C. to 60° C.

* * * * *